United States Patent [19]

Sting et al.

[11] Patent Number: 5,172,182
[45] Date of Patent: Dec. 15, 1992

[54] INTERNAL REFLECTANCE ELEMENT WITH VERY SMALL SAMPLE CONTACTING SURFACE

[76] Inventors: Donald W. Sting, 358 Turtleback Rd., New Canaan, Conn. 06840; John A. Reffner, 97 Ocean Dr. East, Stamford, Conn. 06902

[21] Appl. No.: 708,974

[22] Filed: May 31, 1991

[51] Int. Cl.[5] ............................................. G01N 21/01
[52] U.S. Cl. ................................... 356/244; 356/246; 356/300
[58] Field of Search ................. 356/300, 244, 246, 440

[56] References Cited

U.S. PATENT DOCUMENTS

| | | | |
|---|---|---|---|
| 2,359,787 | 10/1944 | Peters et al. | 250/206 |
| 3,460,893 | 8/1969 | Wilks, Jr. | 356/300 |
| 4,595,833 | 6/1986 | Sting | 250/353 |
| 4,681,451 | 7/1987 | Guerra et al. | 356/373 |
| 4,730,882 | 3/1988 | Messerschmidt | 350/96.1 |
| 4,732,475 | 3/1988 | Harrick | 356/300 |

OTHER PUBLICATIONS

Internal Reflection Spectroscopy: Review and Supplement, Mirabella, Jr., 1985, pp. 98-99.
Review and Supplement, 1985, M. Dekker, Inc. (copy).
U.S. patent appln. Ser. No. 07/622,852 "ATR Objective and Method . . . ".

Primary Examiner—F. L. Evans
Attorney, Agent, or Firm—Calfee, Halter & Griswold

[57] ABSTRACT

An internal reflectance element (IRE), used for internal reflectance spectroscopy (IRS) of solid or liquid samples, has a body including a very small contacting surface adapted to insure contact with a small portion of the sample to improve the spectroscopic analysis of that sample. The contacting surface of the IRE for solids preferably is 100 microns or smaller in diameter and preferably is convexly curved. The contacting surface of the IRE for liquids preferably is 500 microns or smaller. The IRE of the present invention is most frequently used in single internal reflection applications for IRS analysis of solids.

16 Claims, 3 Drawing Sheets

INTERNAL REFLECTANCE ELEMENT WITH VERY SMALL SAMPLE CONTACTING SURFACE

FIELD OF THE INVENTION

The present invention relates to an internal reflection element (IRE), in general, and to an IRE preferably having a curved surface to insure contact with a small portion of a solid or liquid sample being analyzed, in particular.

BACKGROUND OF THE INVENTION

Internal reflectance spectroscopy (IRS) has been accepted as an analytical technique for the analysis of solids and liquids. As a production quality control or a quality assurance method, the IRS analysis of liquids, pastes, mulls, etc. has become quite wide spread. The popularity of using IRS for liquid samples has increased with the acceptance of the Spectra-Tech Circle® cell and horizontal ATR (Contactor ™) accessories. Spectra-Tech's Circle® cell is disclosed in U.S. Pat. No. 4,595,833. Spectra-Tech's horizontal ATR accessory is disclosed in U.S. Pat. No. 4,730,882.

The success of IRS analysis of liquids can, in large part, be attributed to the accuracy, repeatability, precision and reliability of the measurement technique. In addition, for liquids and liquid like materials (i.e., free-flowing "fluids"), IRS is a simple, easy to use method of analysis normally incorporating a multiple bounce radiant energy path. In most cases, however, modest amounts of liquids are required to completely wet the IREs currently in use, which typically have cylindrical contacting surfaces or larger than required flat contacting areas. Specifically, for detection of HPLC, SFC or other eluents, current IRE techniques require the presence of relatively large sample quantities.

For solids, highly reliable, repeatable and photometrically accurate results are not as easily achieved with currently existing apparatus, except for those solids with highly regular, special property surfaces. Since the IRS technique depends upon the electromagnetic coupling of energy within the IRE to the sample in the immediate vicinity (less than 10 microns) of the IRE sample contacting surface, the surface morphology of the sample greatly influences the extent of coupling and the resulting measurements.

Manufacturers of infrared sampling apparatus, as well as users of the IRS technique, have proposed several structures or procedures over the past 20 to 30 years to better insure proper electromagnetic coupling with solid samples. While these techniques may have provided limited improvements in electromagnetic coupling, no general structure or process has gained any widespread acceptance in the industry, especially when quantitative data on solid samples is required.

The following four examples of structure and/or processes to improve electromagnetic coupling of the IRE crystal to the sample are illustrative of some of the prior art techniques. First, the sample can be forced by the application of an evenly distributed pressure against a surface of the IRE. The pressure can be applied pneumatically, hydraulically or mechanically. Second, a high index of refraction oil can be used as a coupling fluid between the sample and the IRE to better match refractive indices through that oil rather than through air. Third, the sample may be heated to soften or recast the material (usually a polymer) onto the sampling surface of the IRE. Fourth, the sample may be dissolved with a solvent so that the resulting liquid can be analyzed and/or an evaporated thin film on the IRE can be analyzed. These IRS solid sampling techniques may be used with many of the known or commercially available IREs.

The books *Internal Reflectance Spectroscopy* (1967, John Wiley & Son, Inc.) and *IRS Review and Supplement* (1985, Marcel Dekker, Inc.) written by Harrick disclosed IRE's for the analysis of materials by using the attenuated total reflectance (ATR) phenomena. These IRE's are generally classified as single internal reflection elements (SIRE) or multiple internal reflection elements (MIRE). The acronym IRE as used herein means both SIRE's and MIRE's.

The known IRE shapes used with liquids include trapezoidally shaped prisms, cylindrical rods and hemispheric domes. IRE's used for IRS analysis of solids include fixed angle prisms and variable angle IRE's including hemicylinders, microhemicylinders, hemispheres with flat bottoms and hemispheres with truncated conical bottoms. On page 98 of the *Internal Reflectance Spectroscopy* book, Harrick illustrates the hemicylinder IRE with flat bottom and the hemispherical IRE with the truncated conical bottom.

In Harrick's noted illustrations, the bottom or sample contacting surface of the IRE is shown to be flat and the sample is shown to be flat. The commercially available IREs for solid sampling are all believed to have flat, sample contacting surface areas of sizes well exceeding 250 microns in diameter.

Harrick categorizes the hemicylinder and hemisphere as variable angle IRE's. Harrick specifies that the angle of incidence is not well defined in these variable IRE's, thereby suggesting that the use of such elements will yield unreliable or non-repeatable results. On page 99 of the Internal Reflectance Spectroscopy book, Harrick explains that a modified hemisphere with a truncated conical flat bottom was used by Fahrenfort to facilitate contacting sample material.

SUMMARY OF THE INVENTION

The commercially available IRE's with relatively large, flat bottom sample surfaces, when placed into contact with the surface of a solid sample, do not insure sufficiently reliable contact to insure consistently repeatable FTIR measurements for "quantitative" evaluation of samples. When applicants changed IRE geometry to have a curved, convex sample contacting surface, repeatability and precision of measurement were dramatically improved.

The principal of a curved sample contacting surface is of most importance to SIRE's used to analyze solids. However, the curved crystal sampling surface can be extended to multiple internal reflection elements and can also be extended to SIRE's used for analyzing liquids.

Applicants have also found by keeping the sample contacting surface less than 500 microns in diameter and preferably less than 100 microns in diameter that repeatability and precision of measurement are improved for curved contacting surfaces and even for small, flat contacting surfaces. With the relatively small sample contacting surface, the sample quantities to be analyzed can be relatively small without jeopardizing the ability to do the analysis, while improving detection accuracy. For example, a droplet of liquid sample can be contacted by a flat sample contacting surface of 100 microns on the IRE to obtain a good engagement interface therebetween to insure reliable electromagnetic coupling. By utilizing a very small sample contacting surface, the force required to insure a good coupling interface is minimized, while signal to noise characteristics for the IRS system are maximized.

In addition, the IRE's with curved sample contacting surface can also be provided with an appropriate optical element to permit visual observation of the sample both before and after its contact with the IRE. The IRS optical system providing visual observation in the survey and viewing modes and radiant energy sampling in an analysis mode is disclosed in U.S. patent application Ser. No. 07/622,852, now U.S. Pat. No. 5,093,580 filed on Dec. 6, 1990. The visual observation of the sample in the survey and viewing modes further leads to improved quantitative results and the repeatability and predictability of those results.

The invention, then, comprises the features hereinafter fully described and particularly pointed out in the claims, the following description and annexed drawings setting forth in detail certain illustrative embodiments of the invention, these being indicative, however, of but a few of the various ways in which the principles of the invention may be embodied.

DETAILED DESCRIPTION OF THE DRAWINGS

Figure 1:
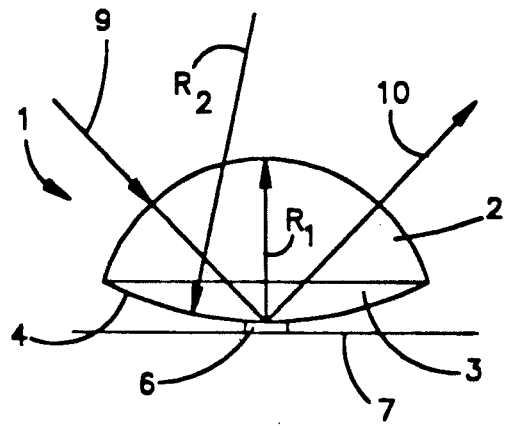
FIG. 1 is an elevation of an SIRE having a curved bottom surface shown in contact with a sample having a flat top surface.

Referring now in more detail to the drawings and initially to FIG. 1, a single internal reflection element (SIRE) consists of a body, indicated generally at 1. The IRE body is preferably a crystal. As illustrated, this body includes a generally hemispherical upper portion 2. An oppositely facing, truncated hemispherical portion 3 is integrally formed therewith. The truncated hemisphere 3 defines a curved, convex sample contacting surface 4. While a curved sample contacting surface of any size is believed to improve IRS analysis, applicants' sample contacting surface is normally kept less than 250 microns in diameter and preferably less than 100 microns in diameter. The relative term "very small contacting surface" as used herein means a circular surface less than 250 microns in diameter or another surface configuration of comparable area.

Radius $R_1$ of the hemispherical portion 2 is selected to match the optical characteristics of the source and detector optics used in conjunction therewith for the IRS spectroscopic analysis. The center of $R_1$ is usually, but not necessarily, at the center of the sampling surface. An example of an exemplary IRS optical system employing a radiant energy source, an IRE and a radiant energy detector are described in U.S. Pat. No. 5,093,580 which is incorporated herein by reference. Radius $R_1$ can be selected utilizing the formula disclosed at page 98 of the *Internal Reflectance Spectroscopy* book or can be selected by utilizing other known optical characteristics of the source and detector.

Radius $R_2$ of the truncated hemisphere is selected to match the illuminated and/or emitting area of the sample to the source and detector sizes (or to any other restricting system aperture) and is further selected to be consistent with the morphology of the sample. The term "morphology" as used herein means exemplary structural characteristics of the solid sample including roughness, flatness, elasticity, hardness, etc. For example, $R_2$ will normally increase for smoother sample areas. On the other hand, $R_2$ will generally decrease as the roughness of the sample increases, depending upon the size of the voids, if any, in that sample.

When used in the IRS objective system illustrated in U.S. Pat. No. 5,093,580, $R_1$ is approximately 3 mm and $R_2$ is approximately 12.85 mm. While the radius $R_2$ is not particularly critical for that objective, it must be sufficiently small to locally contact the "flat area" of the sample, but not so small that the curvature significantly affects the angles of incidence of the impinging radiation. The term "hemisphere" as used herein does not require a full 180° arc and is intended to encompass any arc sufficient to result in the upper portion constituting the major portion of the IRE.

As shown in FIG. 1, the solid sample 6 rests on a sample stage 7. The word "solid" as used herein encompasses any self-supporting substance, with or without voids, and particulates thereof.

The sample stage 7 is preferably movable in the X, Y and Z directions. The stage is elevated so that the top surface of solid sample 6 comes into contact with the convexly curved bottom sample contacting surface 4 of the IRE. Because of the small sample contacting surface area on the IRE, the pressure needed to get the required localized non-destructive surface deformation on the sample is minimized. By having a convexly curved, sample contacting surface 4, the electromagnetic coupling of the IRE to the sample is greatly enhanced in the sampling area to improve the repeatability and predictability of ATR measurement of that sample.

For that purpose, radiant energy 9, such as infrared, is directed into the IRE by the IRS optical system at a selected angle of incidence relative to the sample 6. The radiant energy contacts the curved surface 4 of the IRE and the surface of the sample 6 electromagnetically coupled thereto. Some of the radiant energy will be absorbed into the sample 6 and the rest of the radiant energy is reflected as shown at 10. The reflected radiant energy is returned by the IRS optical system in its encoded form to a detector. The detector can characterize the sample being analyzed by determining what radiant energy was absorbed by the sample.

Figure 2:
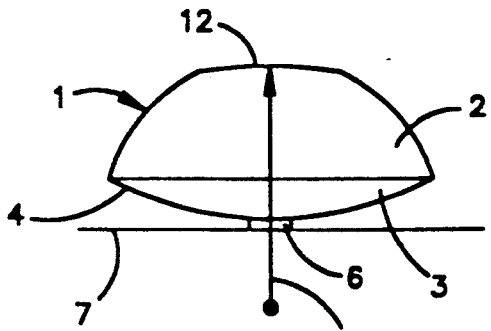
FIG. 2 is an elevation of an SIRE similar in construction to the SIRE in FIG. 1, except a flat or slightly curved area is provided on one side thereof opposite the sample contacting surface.

Turning now to FIG. 2, the IRE shown therein has a body similar to that shown in FIG. 1 except a flat or slightly curved surface 12 is centrally provided thereon adjacent the upper end thereof, opposite the sample contacting surface 4. If the surface 12 is slightly curved, a third radius $R_3$ will be used to define that surface as required by the optics being used and the sample being analyzed.

This flat or curved surface may be used to transmit visible light for visual viewing of the sample both before and after contact with the convexly curved surface 4. Visual observation of the sample through the IRE may also be accomplished with the IRE shown in FIG. 1, with differently configured faces or surfaces on the IRE and with additional optical elements associated with the IRE, such as a lens secured to or positioned proximate the IRE. The visual sample observation through a flat or curved surface, such as 12, is described in U.S. Pat. No. 5,093,580.

Figure 3:
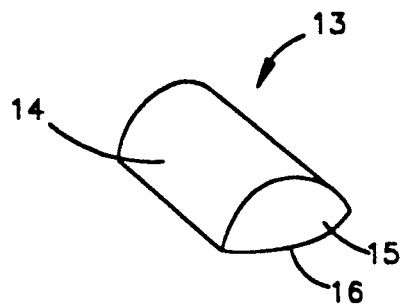
FIG. 3 is a perspective of an SIRE having a generally hemicylinder body with a curved, convex sample contacting surface thereon.

Turning now to FIG. 3, the curved sample contacting surface aspect of the present invention can also be extended to hemicylindrical crystal elements. The SIRE, indicated generally at 13, has a body including a hemicylindrical portion 14 and an oppositely facing truncated hemicylindrical portion 15 integrally formed therewith. The truncated hemicylindrical portion 15 defines a convexly curved sample contacting surface 16.

Figure 4:
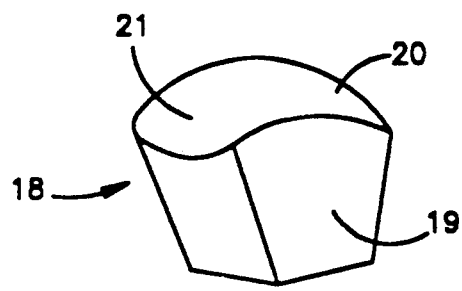
FIG. 4 is a fixed angle SIRE having a curved sample contacting surface.

Turning now to FIG. 4, a single internal reflection crystal element 18 has a body or prism 19 integrally formed with a truncated hemisphere 20 defining a curved sample contacting surface 21. As illustrated, the curved sample contacting surface 21 faces upwardly, although its most frequent use would be in the opposite, downwardly facing direction.

Figure 5:
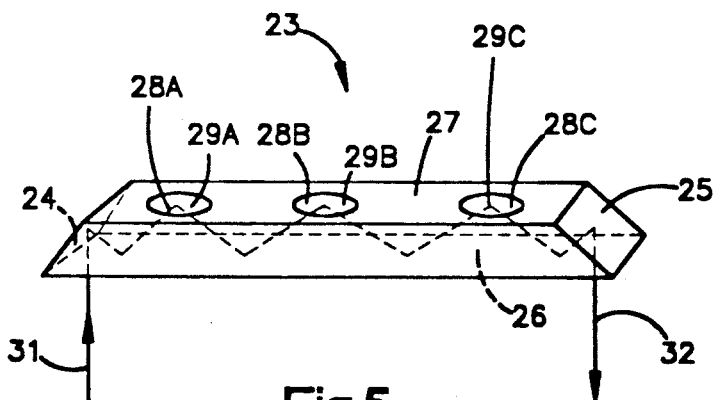
FIG. 5 is a perspective of an MIRE having a plurality of curved sample contacting surfaces in spaced relationship to one another.

Turning now to FIG. 5, the curved sample contacting surface concept of the present invention is illustrated as being extended to a multiple internal reflection element (MIRE) 23. The generally trapezoidally shaped element includes oppositely angled end faces 24 and 25, flat bottom wall 26 and generally flat top wall 27. A plurality of truncated hemispherical portions 28A, 28B and 28C are provided in axially spaced relationship relative to one another along top wall 27. The truncated hemispherical portions 28A, 28B and 28C respectively define three curved sample contacting surfaces 29A, 29B and 29C. The axially spaced truncated hemispheres 28A through 28C are brought into contact with or are contacted by a solid or liquid sample or samples. While the truncated hemispheres are illustrated as facing upwardly in FIG. 5, they would be more frequently used in an opposite, downwardly facing orientation.

In the multiple internal reflection sampling process, radiant energy 31 is brought into MIRE 23 through the bottom wall 26 and then reflects off angled end face 24. This radiant energy then successively reflects off bottom wall 26, truncated hemisphere 28A, bottom wall 26, truncated hemisphere 28B, bottom wall 26, truncated hemisphere 28C and bottom wall 26, as is illustrated by phantom lines showing the multiple internal reflections along the axial length of the MIRE. The radiant energy then leaves the MIRE through the bottom wall after being reflected off the angled end face 25. The emitted radiant energy passing through bottom wall 27 is directed toward the detector in the IRS sampling system, as indicated at 32.

Figure 6:
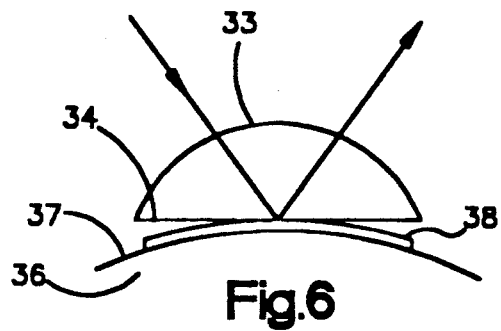
FIG. 6 is an elevation of a hemispherical SIRE having a flat bottom shown in contact with a film placed upon a curved sample stage.

Turning now to FIG. 6, a conventional hemispherical SIRE 33 is illustrated. This conventional hemispherical SIRE 33 has a relatively large, flat sample contacting surface 34. The sample supporting stage 36 has a curved upper surface 37. A solid sample 38, such as a film, is positioned on top of the curved stage surface 37. The film sample 38 is thus curved when it is brought into contact with the flat sample contacting surface 34 of SIRE 33. In one of its broadest contexts, the present invention covers either a curved sample contacting surface on the IRE or a curved solid sample surface contacting the crystal. As long as one of these two elements is curved, more reliable crystal to sample contact will be made to enhance the electromagnetic coupling therebetween.

Figure 7:
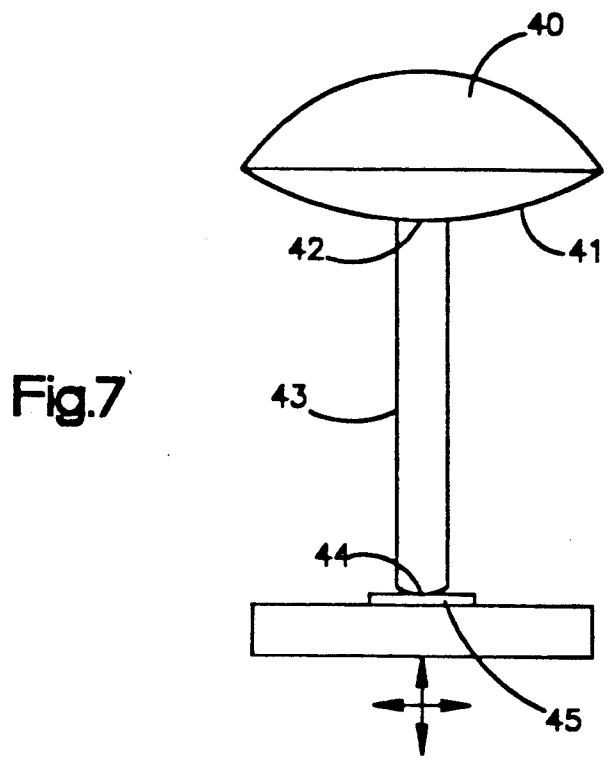
FIG. 7 is an elevation of a hemispherical SIRE having the curved bottom surface thereof in contact with a complementally curved end of a fiber optic waveguide extending to the sample.

Turning now to FIG. 7, a hemispheric SIRE 40 is illustrated having an oppositely facing, truncated hemispherical portion thereon to define a curved sample contacting surface 41. One end 42 of a fiber optic waveguide 43 is brought into contact with the curved sample contacting surface 41. The end 42 of the fiber optic waveguide 43 is complementally curved to provide good surface contact between the fiber optic waveguide end and the IRE contacting surface 41. The other end 44 of the fiber optic waveguide 43 has the same curve as end 42 and curved surface 41. The curved end 44 of the fiber optic waveguide 43 contacts the upper surface of the solid sample 45. The radiant energy is transmitted into crystal 39, along fiber optic waveguide 43 to sample 45, and then returns through fiber optic waveguide 43 and SIRE 39 to a radiant energy detector. A fiber optic waveguide can be used when the configuration of the instrument or the configuration of the sample requires an optical extension of the system.

Figure 8:
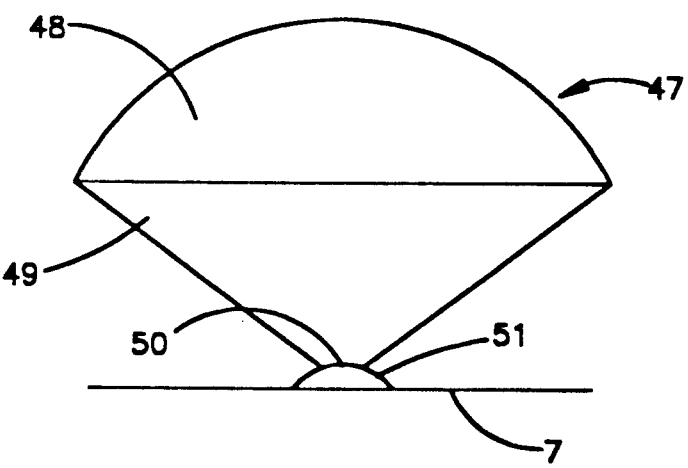
FIG. 8 is an enlarged elevation of a single bounce IRE having a very small, flat sample contacting surface in engagement with a small portion of a liquid sample droplet.

Turning now to FIG. 8, the IRE body, indicated generally at 47, includes a hemispherical portion 48 and a truncated conical portion 49 integrally formed therewith. The truncation of the cone defines at the tip thereof a bottom sample contacting surface 50. This bottom sample contacting surface may be flat, although a convexly curved surface is still preferred. The sample contacting surface is very small, preferably less than 500 microns in diameter. The surface 50 is in contact with a small portion of a drop 51 of a liquid sample supported on sample stage 7. The area of interface contact will insure good electromagnetic coupling between the IRE body 47 and the sample liquid 51, even though only a drop of liquid is available for analysis purposes.

Figure 9:
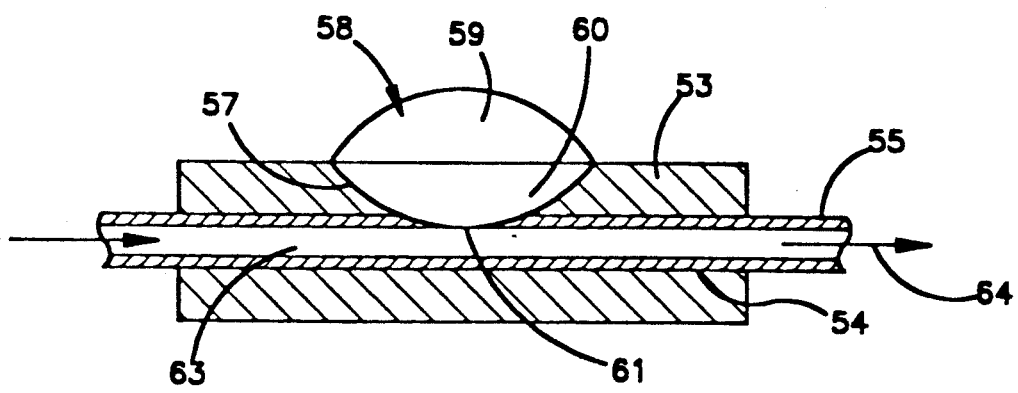
FIG. 9 is a vertical side view cross section of an IRE mounted in and partially extending through the wall of a tube to place the curved sample contacting surface of the IRE in contact with fluid contained in the tube for IRS analysis of that fluid.

Turning now to FIG. 9, a mounting block 53 has a bore 54 passing therethrough. A small bore tube 55, such as a stainless steel HPLC tube having a diameter of 0.1 millimeter, is partially received in bore 54 and extends through and beyond mounting block 53. The block 53 and part of the wall of tube 55 are machined to form a truncated hemispherical socket 57 that extends to the inner diameter of that tube. The socket 57 is dimensioned to tightly receive an IRE, indicated generally at 58, having a hemispherical main portion 59 and a truncated hemispherical bottom portion 60.

The truncated hemispherical portion is sealed to mounting block 53 and tube 55 and defines a very small, convexly curved sample contacting surface 61 that faces and is exposed to the bore of tube 55. A fluid 63 may be contained in or may pass through tube 55, as schematically indicated by arrows 64. This fluid can be analyzed by IRS techniques because the very small sample contacting surface 61 of IRE 58 is in intimate contact with the fluid in tube 55.

Figure 10:
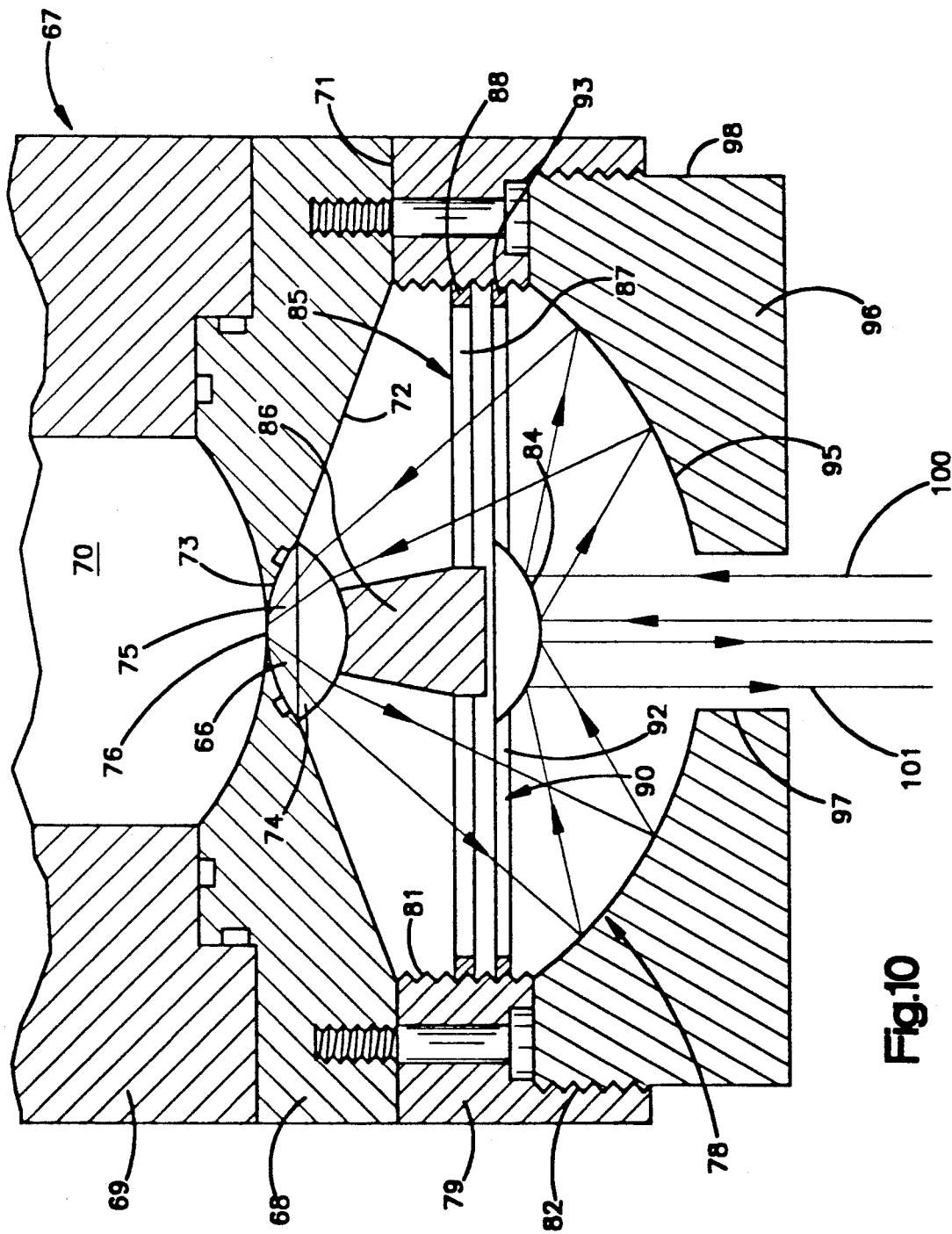
FIG. 10 is a vertical cross section showing an IRE mounted in the base of a reactor flask, with the curved sample contacting surface thereof being in contact with the fluid contained in the reactor flask.

Turning now to FIG. 10, an IRE, indicated generally at 66, is mounted for IRS analyzation of fluids contained in a reaction vessel, indicated generally at 67. The reaction vessel includes a base 68, a generally cylindrical side wall 69 sealed to the base, and a top (not shown). The base 68, side wall 69 and top cooperate to define therewithin a reaction chamber 70, which contains the fluid to be analyzed.

The base 68 has a bottom surface, which includes an annular outer flange 71 and a generally conical inner surface 72. A truncated hemispherical socket 73 extends into and partially through the center portion of the base 78. The IRE is received in and sealed to the socket 73.

The IRE includes a hemispherical portion 74 and a truncated hemispherical portion 75 integrally formed therewith. The truncated hemispherical portion defines a convex curved surface, a very small portion 76 of which is exposed to the chamber 70 and in intimate contact with any fluid contained therein. This very small sample contacting surface 76 allows IRS analysis of any fluid contained in chamber 70 by using the IRS optical system, indicated generally at 78.

The IRS optical system includes an annular adjustment sleeve 79 removably secured to the bottom of flange 71 on base 68 of the reactor vessel 67. The adjustment sleeve 79 includes a threaded bore 81 and a threaded counter bore 82. The threaded bore 81 may be used to vertically adjust the IRE 66 and a secondary mirror 84.

Initially with respect to the IRE, it can be permanently mounted in and sealed to the socket 73, if desired. Alternatively, if different IRE's are to be used from time to time or if one IRE is going to be periodically removed, cleaned and then replaced, a vertical adjustment and retention means can be provided for this purpose.

As shown, a first spider assembly, indicated generally at 85, includes a central pusher block 86, a plurality of circumferentially spaced spiders or spokes 87 radially emanating from and connected to pusher block 86, and a first annular adjustment ring 88 extending circumferentially around and being connected to the outer ends of spokes 87. The outer diameter of first adjustment ring 88 has threads thereon which mate with the threads on the inner diameter of bore 81. The upper end of the pusher block 86 is in abutment with or secured to the central portion of the bottom curved surface on hemispherical portion 74 of IRE 66. The rest of the curved bottom surface of hemispherical portion 74 is exposed between the pusher block 8 and the conical bottom surface 72 of base 68.

By rotating first ring 88 in the proper direction, the spokes 87 and pusher block 86 connected thereto will be elevated to lift IRE 66 into socket 73 for sealing contact therewith. Alternately, ring 88 can be rotated in the reverse direction to lower the spokes 87 and pusher block 86 connected thereto to withdraw IRE 66 from socket 73 for replacement or cleaning of the IRE 66.

With respect to the secondary mirror, it can be mounted on the bottom of pusher block 86. However, to relieve stress in the secondary mirror and to permit relative adjustment of the secondary mirror for prealigning the optics, a second spider assembly indicated generally at 90, may be provided.

The second spider assembly 90 includes circumferentially spaced spiders or spokes 91 connected to and extending radially outwardly from secondary mirror 84. The radially outer ends of spokes 92 are connected to a second annular adjustment ring 93. Threads on the outer diameter of second adjustment ring 93 mate with the threads on bore 81 of annular sleeve 79. By rotating second adjustment ring 93 for vertical movement in either direction along threads 81, the secondary optic 84 can be selectively raised or lowered as required for prealignment of the optics in the IRS system.

The IRS optical system includes a primary mirror 95 provided on the inner side of primary block 96. Primary block 96 has a central opening 97 therethrough to allow radiant energy to enter and exit the optical system. The outer annular wall 98 of primary block 96 has threads thereon which mate with the threads on counterbore 82. This threaded connection allows the primary block 96 to be vertically raised or lowered by primary block rotation in one direction or the other, thereby to permit prealignment of the hemispherical primary mirror 95 in the optical path.

In operation, radiant energy from a radiant energy source passes through opening 97, as indicated by the arrows 100. This radiant energy sequentially reflects off secondary mirror 84 and primary mirror 95. The incident radiant energy then passes through the IRE element against the very small sample contacting surface 76, which is in contact with the fluid contained in the reaction vessel 67. Radiant energy, which is not absorbed by the fluid sample, is reflected off the very small sample contacting surface 76 and is emitted from the IRE 66. This emitted radiant energy sequentially reflects off primary mirror 95 and secondary mirror 84. The emitted energy then passes through opening 97 (as indicated by arrows 101) and is subsequently directed to a detector for IRS analysis of the fluid.

It will be apparent from the foregoing that changes may be made in the details of construction and configuration without departing from the spirit of the invention as defined in the following claims.

We claim:

1. An internal reflection element comprising a body including at least one curved surface having a diameter of 500 microns or less placed in contact with a sample to obtain electromagnetic coupling therewith at a selected area of interest to enhance internal reflectance spectroscopic analysis of the sample.

2. The internal reflection element of claim 1 wherein the curved sample contacting surface is a truncated hemisphere having a convex shape.

3. The internal reflection element of claim 2 wherein the body is an integral combination of a hemisphere on one side and the truncated hemisphere on the other side.

4. The internal reflection element of claim 3 wherein a radius, $R_1$, for the hemisphere is selected to be optically compatible with optical characteristics of a radiant energy source and detector used in conjunction with the internal reflection element for spectroscopic analysis of the sample.

5. The internal reflection element of claim 4 wherein a radius, $R_2$, for the truncated hemisphere, is selected to be compatible with sample morphology and with the size of the sample area being analyzed.

6. The internal reflection element of claim 5 wherein a flat or slightly curved surface is provided on the hemisphere for visual observation of the sample.

7. The internal reflection element of claim 1 wherein the body is a prism and a plurality of curved sample contacting surfaces are provided along one side of the prism in spaced relationship to one another for multiple internal reflections of energy along the prism.

8. The internal reflection element of claim 1 wherein the body is a prism.

9. The internal reflection element of claim 8 wherein the body is an integral combination of a hemicylinder and an oppositely facing truncated hemicylinder comprising the sample contacting surface.

10. The internal reflection element of claim 1 wherein the sample is a solid and the curved surface is less than 150 microns in diameter.

11. The internal reflection element of claim 10 wherein the curved surface is less than 100 microns in diameter.

12. The internal reflection element of claim 1 wherein the sample is held against the curved sample contacting surface by a movable stage which applies pressure to the sample to obtain localized contact or non-destructive surface deformation of the sample to enhance the electromagnetic coupling at the selected area of interest.

13. An internal reflection element comprising a body having a sample contacting surface in contact with a small portion of a sample to obtain good electromagnetic coupling therebetween for internal reflectance spectroscopic analysis of that sample, the sample being held against the sample contacting surface by a convexly curved member, said small portion of contact having a generally circular area and said sample contacting surface being less than 500 microns in diameter.

14. The internal reflection element of claim 13 wherein the sample contacting surface is less than 100 microns in diameter and is convexly curved.

15. The internal reflection element of claim 13 wherein the sample contacting surface is flat.

16. An internal reflection element including a body having a first curved surface and a fiber optic wave guide, a first end of said wave guide having a second curved surface in contact with and of substantially the same radius as the first curved surface, and a second end of said wave guide having a third curved surface of substantially the same radius as the first and second curved surfaces, the third curved surface being in contact with a sample surface to obtain electromagnetic contact therewith at a selected area of interest to enhance internal reflectance spectroscopic analysis of the sample.

* * * * *